United States Patent [19]

Pavcnik et al.

[11] Patent Number: 5,643,317
[45] Date of Patent: Jul. 1, 1997

[54] CLOSURE PROSTHESIS FOR TRANSCATHETER PLACEMENT

[75] Inventors: Dusan Pavcnik, Nova Gorica, Slovenia; Sidney Wallace; Kenneth C. Wright, both of Houston, Tex.

[73] Assignee: William Cook Europe S.A., Bjaeverskov, Denmark

[21] Appl. No.: 244,580

[22] PCT Filed: Nov. 25, 1992

[86] PCT No.: PCT/US92/10141

§ 371 Date: May 27, 1994

§ 102(e) Date: May 27, 1994

[87] PCT Pub. No.: WO93/10714

PCT Pub. Date: Jun. 10, 1993

[51] Int. Cl.⁶ .................................. A61B 17/08
[52] U.S. Cl. .......................... 606/213; 606/151
[58] Field of Search ................ 606/1, 151, 190, 606/198, 213, 215; 604/11, 13, 15, 16; 128/20, 830–839

[56] References Cited

U.S. PATENT DOCUMENTS

| | | |
|---|---|---|
| 3,874,388 | 4/1975 | King et al. . |
| 4,007,743 | 2/1977 | Blake . |
| 4,744,364 | 5/1988 | Kensey . |
| 4,852,568 | 8/1989 | Kensey . |
| 4,890,612 | 1/1990 | Kensey . |
| 5,041,093 | 8/1991 | Chu . |
| 5,108,420 | 4/1992 | Marks .................... 606/213 |
| 5,254,133 | 10/1993 | Seid ........................ 606/151 |

OTHER PUBLICATIONS

William J. Rashkind, M.D., Charles E. Mullins, M.D., Willam E. Hellenbrand, M.D., and Mary Angela Tait, B.S., *Nonsurgical Closure of Patent Ductus Arteriosus: Clinical Application of the Rashkind PDA Occluder System*, Circulation, vol. 74, No. 3, p. 583, Mar. 1987.

James E. Lock, M.D., John T. Cockerham, M.D., John F. Keane, M.D., John P. Filey, M.D., Paul E. Wakely, Jr., M.D., and Kenneth E. Fellows, M.D., *Transcatheter Umbrella Closure of Congenital Heart Defects*, Circulation, vol. 75, No. 3, p. 593, Mar. 1987.

E.B. Sideris, M.D., S.E. Sideris, R.N., J.P. Fowlkes, RDMS, R.L. Ehly, RT, J.E. Smith, R.N. and R.E. Guide, M.D., *Transvenous Atrial Spetal Defect Occlusion in Piglets With a "Buttoned" Double–Disk Device*, Jan., Circulation, vol. 81, No. 1, pp. 314 and 312, 1990.

Jonathan J. Rome, M.D., John F. Keane, M.D., Stanton B. Perry, M.D., Philip J. Spevak, M.D., and James E. Lock, M.D., *Double–Umbrella Closure of Atrial Defects*, Circulation, vol. 82, No. 3, p. 751, Sep. 1990.

Albert P. Rocchni, M.D., *Transcatheter Closure of Atrial Septal Defects*, Circulation, vol. 82, p. 1044, 1990.

Toshio Yamaguchi, Haruhito Fukuoka, Kazuo Yamamoto, Shizutomo Katsuta, and Mitsushige Ohta, *Transfemoral Closure of Patent Ductus Arteriosus: An Alternative to Surgery in Older Patients*, CardioVascular and Interventional Radiology, p. 291, 1990.

*New Technique for Transcatheter Closure of Patent Ductus Arteriosus*, p. 156.

Primary Examiner—Glenn Dawson
Attorney, Agent, or Firm—Woodard, Emhardt, Naughton, Moriarty & McNett

[57] ABSTRACT

A closure prosthesis and transcatheter delivery system includes a closure prosthesis for sealing across all opening of a fluid passageway within a living body. The closure prosthesis is a flexible disk including a flexible ring and diaphragm having a plurality of hollow flexible wire segments attached thereto. Delivery of the closure prosthesis is accomplished using a hollow sheath and a pusher catheter slidable within the sheath, wherein filaments are looped through the wire segments to releasably connect the disk to the pusher catheter. The disk is resiliently compressed within the sheath and, upon release therefrom, the disk resiliently expands into a larger, unrestrained shape. Tension applied to the filaments resiliently bends the wire segments so that they may be drawn through the opening of the defect. Upon releasing the filaments from the disk, the wire segments resiliently expand to trap the disk in place to seal across the opening.

19 Claims, 6 Drawing Sheets

CLOSURE PROSTHESIS FOR TRANSCATHETER PLACEMENT

BACKGROUND OF THE INVENTION

This invention relates in general to closure prostheses which might find application for transcatheter placement within the heart to close congenital and operative cardiovascular defects.

Examples of such cardiovascular defects include those which result in an abnormal opening in the cardiovascular system and permit deleterious shunting of blood thereacross, such as atrial and ventricle septum defects and patent ductus arteriosus. To minimize the risk of mortality associated with surgery, transcatheter techniques have been developed to introduce closure devices for sealing such defects. One example of such a device is described in Blake, U.S. Pat. No. 4,007,743. Blake discloses a pair of umbrella-like closure devices which include resilient ring sections to automatically open the struts of the umbrella as the devices are pushed out of their respective catheters. King et al., U.S. Pat. No. 3,874,388, similarly discloses a pair of umbrella-like closure devices which interconnect after placement to seal across a defect.

These and other such devices rely on the caudal and cranial ends of the device being larger than the opening of the defect itself to physically trap the device across the opening. To accommodate transcatheter delivery techniques, the resulting device configurations have become unduly mechanical in nature, often including multiple components or requiring sequential delivery. Also, many of these devices require assembly across the defect after delivery, thereby increasing the complexity of the transcatheter equipment and delivery process.

A need therefore exists for an improved closure device. Such a device would be of a compact, unitary construction, therefore permitting the device to be delivered intact using transcatheter techniques. Also, such a device would be delivered from a sheath or catheter in a one-step procedure, rather than requiring sequential delivery. Similarly, such a device would be manually controlled after delivery to ensure proper placement and sealing across the defect. Preferably, the device would also be self-centering to facilitate proper delivery and placement across the defect.

SUMMARY OF THE INVENTION

A flexible closure prosthesis and transcatheter delivery system are disclosed, wherein the closure prosthesis seals across an opening of a fluid passageway within a living body. The closure prosthesis includes a flexible sealing element and a flexible restraining element attached to the sealing element. Delivery of the closure prosthesis is accomplished using a hollow sheath and a pusher catheter slidable within the sheath. Filament means are employed for resiliently bending the closure prosthesis, wherein the filament means releasably connect the closure prosthesis to the pusher catheter. The closure prosthesis is resiliently compressible into a first insertion form constrained within the sheath for placement adjacent the opening, wherein the closure prosthesis resiliently expands after release from the sheath into a first larger form. The closure prosthesis is resiliently compressible into a second insertion form constrained by the filament means for placement across the opening, wherein the closure prosthesis resiliently expands after release from the filament means into a second larger operational form and wherein the sealing element seals across the opening and the restraining element restrains the closure prosthesis in place across the opening.

A method for delivering a closure prosthesis is also disclosed, including the steps of connecting a closure prosthesis to a pusher catheter, inserting the closure prosthesis and the pusher catheter into a sheath adjacent the opening, the closure prosthesis resiliently compressing into a first insertion form constrained within the sheath, releasing the closure prosthesis from the sheath, the closure prosthesis resiliently expanding into a first larger form adjacent the opening, resiliently compressing the closure prosthesis into a second insertion form, the restraining element being resiliently compressed to permit passage thereof through the opening, and releasing the closure prosthesis from the pusher catheter, wherein the closure prosthesis expands into a second larger operational form in which the sealing element seals across the opening and the restraining element restrains the closure prosthesis in place across the opening.

One object of the present invention is to provide an improved closure prosthesis and delivery system adapted thereto.

Another object of the present invention is to provide a closure prosthesis having a compact, unitary construction permitting the device to be delivered intact using transcatheter techniques.

Another object of the present invention is to provide a closure prosthesis which is delivered from a sheath or catheter using a one-step procedure.

Another object of the present invention is to provide a closure prosthesis which can be manually controlled after delivery to ensure proper placement and sealing across the defect.

Still another object of the present invention is to provide a closure prosthesis which is self-centering.

Related objects and advantages of the present invention will become apparent from the following description.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
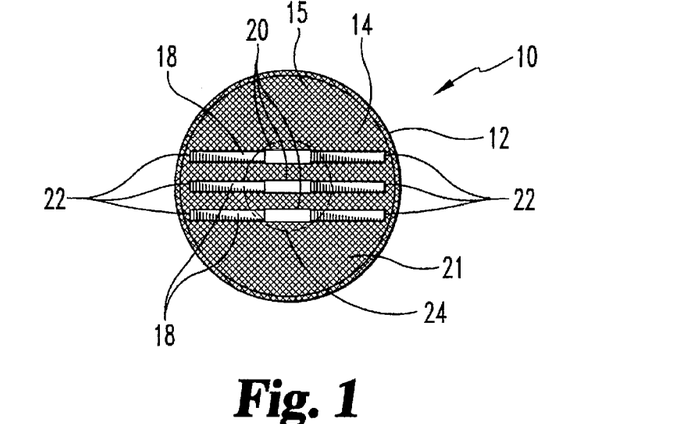
FIG. 1 is a rear elevational view of a disk prosthesis according to one embodiment of tile present invention.
Figure 2:
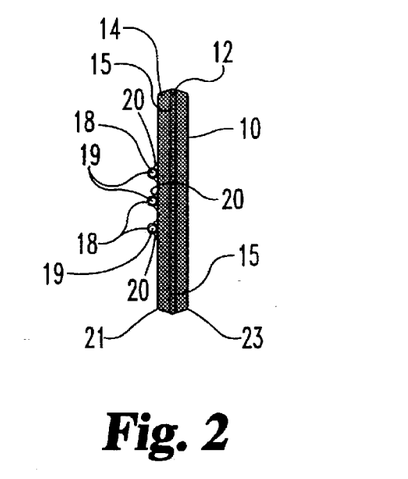
FIG. 2 is a side elevational view of the disk prosthesis shown in FIG. 1.

Referring now to FIGS. 1 and 2, a flexible disk 10 is shown including a flexible ring 12 covered by diaphragm 14. Disk 10 is resiliently compressible so as to flex when restrained into a smaller form to facilitate insertion and placement thereof, wherein when compressed disk 10 resiliently bends without permanent deformation to store energy therein. Unrestrained, disk 10 resiliently expands into a larger operational form by releasing the energy stored therein, wherein disk 10 resiliently unbends without permanent deformation to its original form.

Diaphragm 14 attaches to ring 12 and functions to seal across ring 12. Therefore, flexible ring 12 and diaphragm 14 attached thereto define a sealing element sized to seal across an opening of a cardiovascular defect. Other shaped flexible sealing elements in addition to disk shapes are contemplated as well, wherein the sealing element conforms to the shape of the defect. Similarly, other constructions of sealing elements are contemplated, such as a flexible ring with only one diaphragm or an integral ring and diaphragm constructed of a resiliently flexible material.

Attached to diaphragm 14 are flexible wire segments 18 for trapping the disk in place. As such, flexible wire segments 18 define a restraining element sized to restrain the disk across the defective opening. Flexible ring 12 is sized to a diameter larger than that of the opening, and wire segments 18 are similarly of a length greater than the defect diameter. Wire segments 18 are hollow cylinders and include openings 19 extending longitudinally therethrough. Wire segments 18 are attached along a portion of their length to the central portion of diaphragm 14 at attachment points 20, thereby defining free ends 22 of wire segments 18 at either side of the attachment points which are detached from diaphragm 14 and free to flex outwardly from disk 10. Attachment points 20 of wire segments 18 to diaphragm 14 collectively define an attachment zone 24, as depicted by the dashed lines in FIG. 1. Because the free ends of wire segments 18 are pulled outwardly from the disk into a smaller form to pass through the defect opening during deployment as shown in FIGS. 8 through 11, attachment zone 24 should be sized smaller than the defect opening. Other flexible restraining element configurations in addition to flexible wire segments are contemplated as well, such as overlapping flexible tabs or ears with openings therethrough which when resiliently bent into a smaller form define an attachment zone sufficiently small to pass through a defect opening.

In one embodiment of the present invention, flexible ring 12 is constructed of 0.025 to 0.028 inch diameter stainless steel coil wire formed into a ring and having an overall diameter of 2 cm. As such, in this embodiment disk 10 is capable of sealing an opening of up to 2 cm. in diameter; however, to provide a margin of safety, in this embodiment disk 10 seals an opening of approximately 1.5 cm. in diameter. Ring 12 is covered by a double wall nylon mesh material including nylon meshes 21 and 23 containing a nylon foam core 15 within ring 12 to define diaphragm 14, wherein the nylon mesh is threaded onto the ring to attach thereto to trap the foam core in place and the foam core functions to substantially seal across ring 12.

Three lengths of 0.032 to 0.035 inch diameter stainless steel coil wire are attached along the mid-portions of their lengths to diaphragm 14. Attachment techniques common to the industry are employed depending on the size and operational characteristics of the disk to be deployed. For example, wire segments 18 can be looped or threaded through a portion of the nylon mesh forming diaphragm 14. In another embodiment depicted in FIG. 3, flexible ring 12 includes flexible elements 13 for added structure and resiliency. Flexible elements 13 are formed by attaching two lengths of elastic filament to ring 12. In this embodiment, the elastic filaments are constructed of rubber or an equivalent material and are tied to ring 12 using nylon filament ties. Ring 12 further includes two to three loops 12a of 0.010 inch diameter stainless steel safety wire inside its 0.025 to 0.028 inch diameter for added resiliency to maintain its circular shape.

Figure 3:
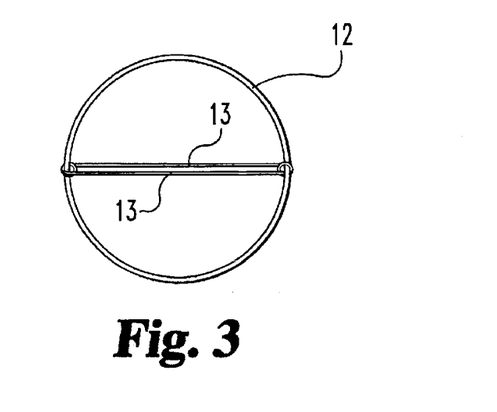
FIG. 3 is an elevational view of a flexible ring of a disk prosthesis having flexible elements attached thereto according to another embodiment of the present invention.
Figure 4:
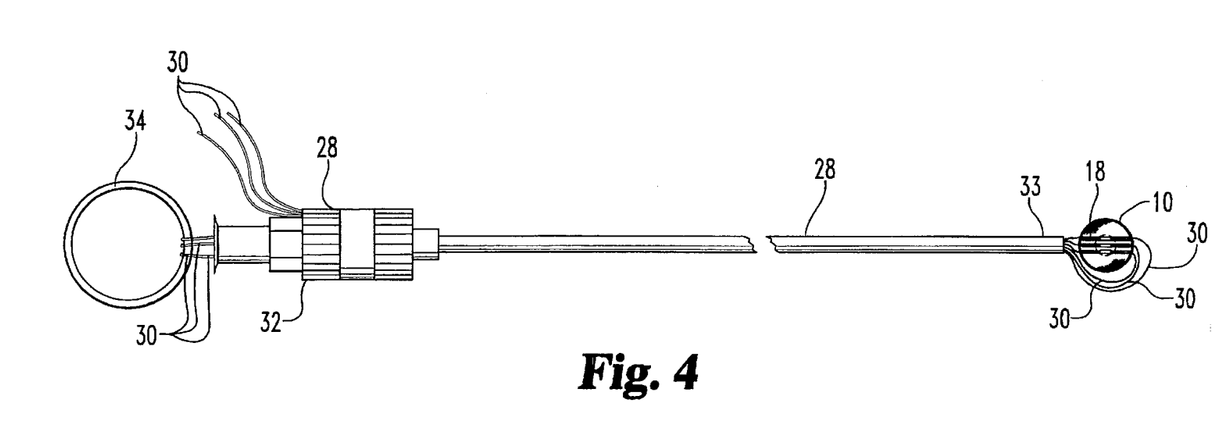
FIG. 4 is a side elevational view of a pusher catheter connected by filaments to the disk prosthesis of FIG. 1 according to another embodiment of the present invention.
Figure 5:
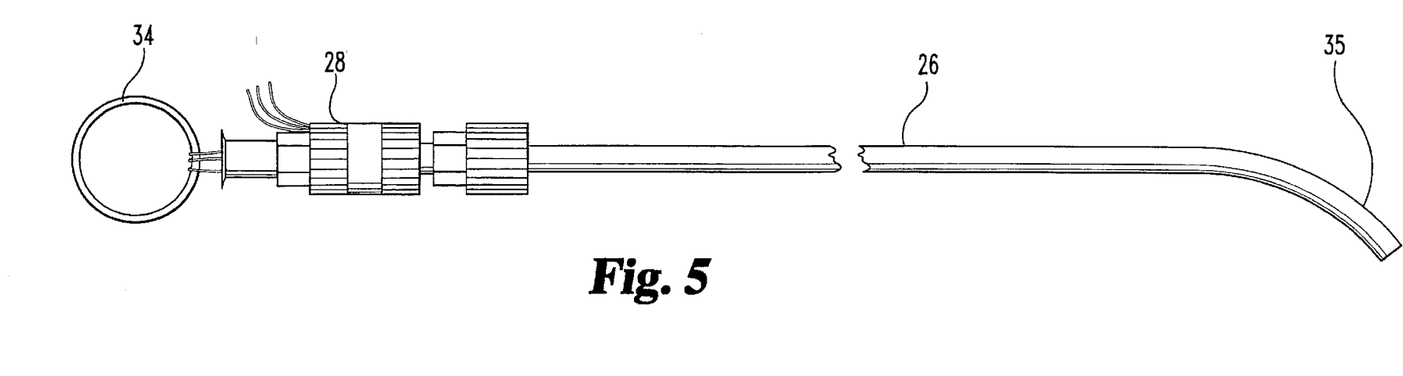
FIG. 5 is a side elevational view of an introducer sheath assembly containing the pusher catheter and disk prosthesis of FIG. 4 therein.

Multiple foam cores are contemplated on either side of flexible elements 13, wherein a nylon mesh is similarly attached to ring 12 to trap the foam cores in place to substantially seal across ring 12. Fasteners and adhesives may also be employed either to attach the wire segments to the diaphragm or to provide a redundant attachment for improved margins of safety over existing attachments. As shown in FIGS. 4 and 5, disk 10 is capable of percutaneous insertion via an introducer sheath assembly 26 and employing a pusher catheter 28. Sheath assembly 26 is adapted to insert into the femoral vein, extending into the heart and providing a pathway for positioning disk 10 adjacent a defect. Delivery of the sheath may be accomplished according to standard medical procedures. One delivery scheme might include inserting a wire guide through a needle and positioning the wire guide adjacent the defect. The sheath assembly with a dilator can be inserted over the wire guide, wherein the wire guide and dilator are then removed leaving the sheath assembly in place. In one embodiment, a 9 F sheath assembly is used in conjunction with a 7 F pusher catheter, wherein the sheath assembly is 80 cm. long and the pusher catheter is slightly longer at 81 cm. Disk 10 is resiliently collapsible along the longitudinal axis of wire segments 18 into a smaller cross-sectional shape for insertion within sheath assembly 26. As depicted in FIG. 4, disk 10 is connected to pusher catheter 28 via filaments 30 prior to insertion within sheath assembly 26. A number of filament lengths greater than or equal to the number of wire segments 18 of disk 10 are used, wherein each length of filament is sufficiently long and of reduced diameter to pass through catheter 28 and wire segments 18. In one embodiment, filaments 30 are 0.008 inch diameter nylon filament, each approximately 3 meters in length. Each of filaments 30 are attached at one of their ends to proximal end 32 of catheter 28. Each filament is routed through and exits the distal end 33 of catheter 28, through openings 19 of wire segments 18, and returns through catheter 28 to attach to ring 34. Ring 34 is larger than catheter 28 to prevent filaments 30 from retracting into the catheter. As such, ring 34 will abut catheter 28 when released to prevent slackened filaments 30 from retracting into the catheter. Conversely, pulling ring 34 away from catheter 28 takes up slack in filaments 30 until disk 10 abuts the distal end 33 of catheter 28. Further pulling of ring 34 tightens filaments 30 and pulls free ends 22 of wire segments 18 away from disk 10.

Figure 6:
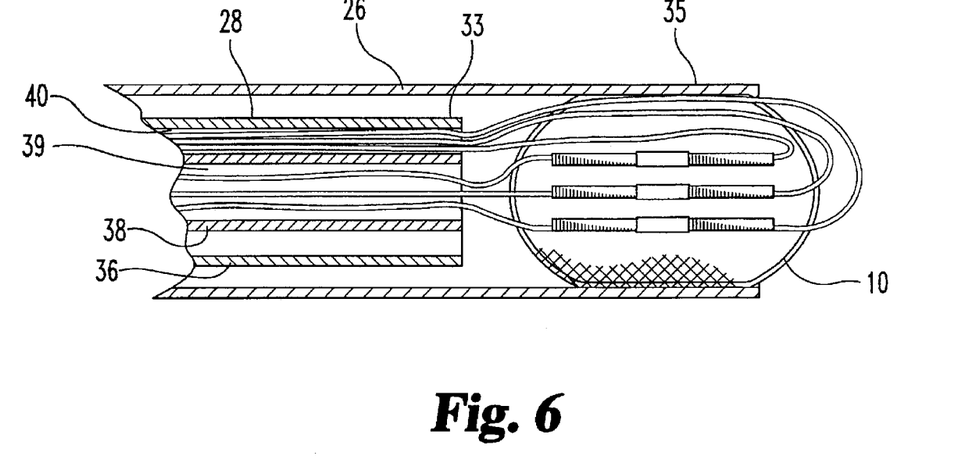
FIG. 6 is an exploded cross-sectional view of the distal end of the sheath assembly of FIG. 5.
Figure 7:
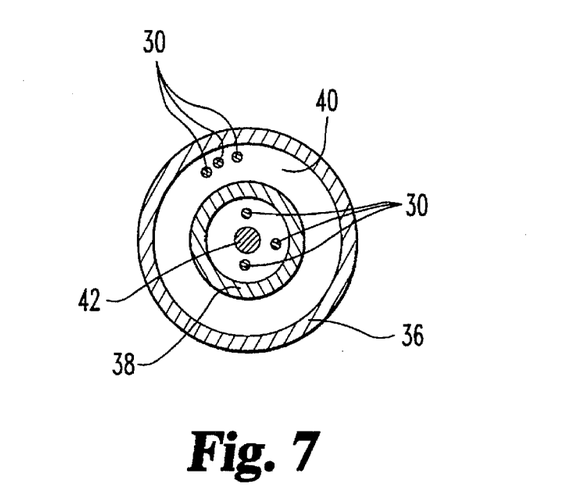
FIG. 7 is a cross-sectional view of the pusher catheter of FIG. 4 and including a wire guide according to another embodiment of the present invention.
Figure 8:
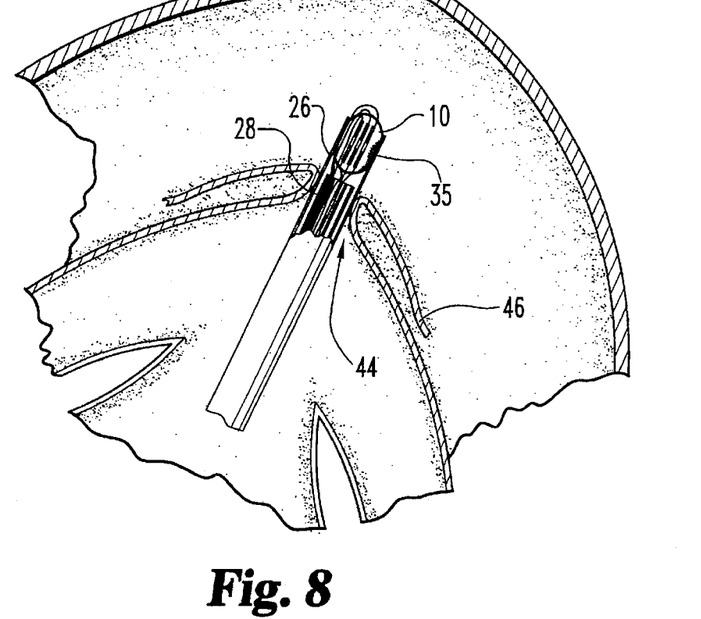
FIG. 8 is a partial cross-sectional view of the distal end of the introducer sheath assembly of FIG. 5 inserted and extending through a cardiovascular defect.
Figure 9:
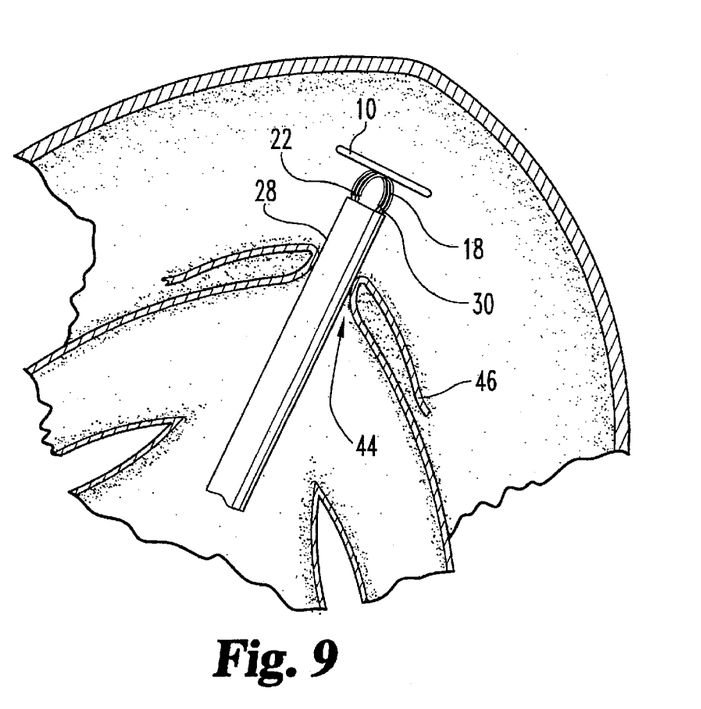
FIG. 9 is a partial cross-sectional view of the distal end of the pusher catheter of FIG. 4 inserted and extending through a cardiovascular defect with the disk prosthesis drawn tight against the catheter.
Figure 10:
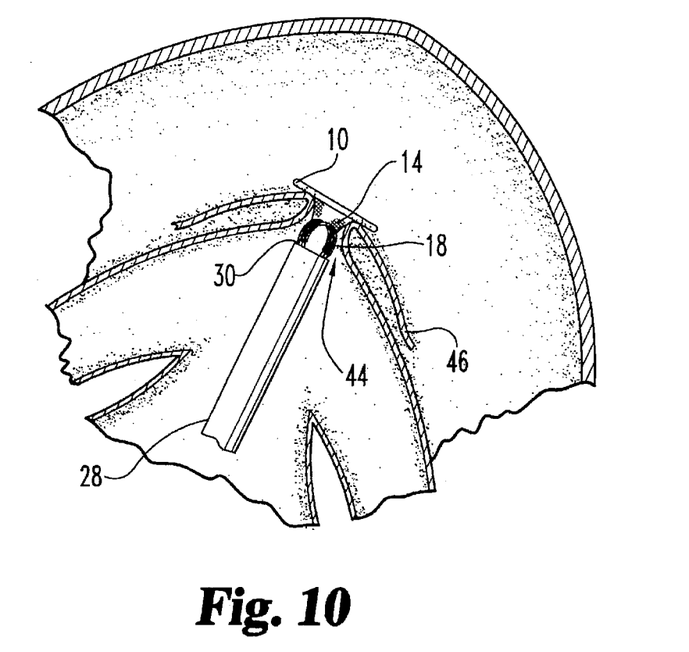
FIG. 10 is a partial cross-sectional view of the distal end of the pusher catheter of FIG. 4 adjacent a cardiovascular defect with the disk prosthesis seated against the vessel walls of the defect.

Referring now to FIG. 6, an exploded cross-sectional view of the distal end 33 of catheter 28 is shown, with disk 10 connected thereto by filaments 30 and compressed within the distal end 35 of sheath assembly 26 prior to delivery. Catheter 28 is a double-lumen catheter including an inner catheter 38 and an outer catheter 36. The bore of inner catheter 38 defines inner lumen 39, wherein the annulus formed between inner catheter 38 end outer catheter 36 defines outer lumen 40. In one embodiment, the inner catheter is a 5 F catheter and the outer catheter is a 7 F catheter. Filaments 30 pass through outer lumen 40 as they extend from the proximal end 32 of catheter 28 through to wire segments 18 of disk 10. Filaments 30 return through inner lumen 39 to exit therefrom and attach to ring 34. Therefore, as shown in FIG. 7, filaments 30 are separated from each other by inner catheter 38 as they extend in opposing directions through catheter 28, thereby reducing risk of entanglement. Nevertheless, catheter 28 is also contemplated as a single lumen catheter to permit further reductions in the size of the transcatheter delivery system. Also contemplated is a wire guide 42 disposed within inner catheter 38 to aid in maintaining the inner lumen open, as shown in FIG. 7. Referring now to FIGS. 8 through 11, the delivery of disk 10 is depicted adapted to closing a defect such as a patent ductus arteriosus. In FIG. 8, sheath assembly 26 is shown with its distal end 35 projecting through defect opening 44, with disk 10 resiliently compressed into a first insertion form and constrained by the sheath assembly prior to delivery. Disk 10 is delivered by pulling back sheath assembly 26 while holding catheter 28 in place and, as the sheath assembly is withdrawn to expose and release the disk, disk 10 resiliently self-expands to its unrestrained larger operational form. As discussed previously, ring 34 is then pulled outwardly from catheter 28 to take up slack in filaments 30. Due to this motion, disk 10 will abut the distal end of catheter 28 at one or more free ends 22 of wire segments 18, at which point further tightening of filaments 30 results in the wire segments being resiliently compressed and pulled away from disk 10. As such, a second insertion form is defined permitting the wire segments to be withdrawn through to the side of the defect opposite the disk as shown in FIGS. 9 and 10. As shown in FIG. 10, after the wire segments are withdrawn through the defect, catheter 28 is pulled back from the defect, further tightening filaments 30, to effectively seat the disk against vessel walls 46.

Figure 11:
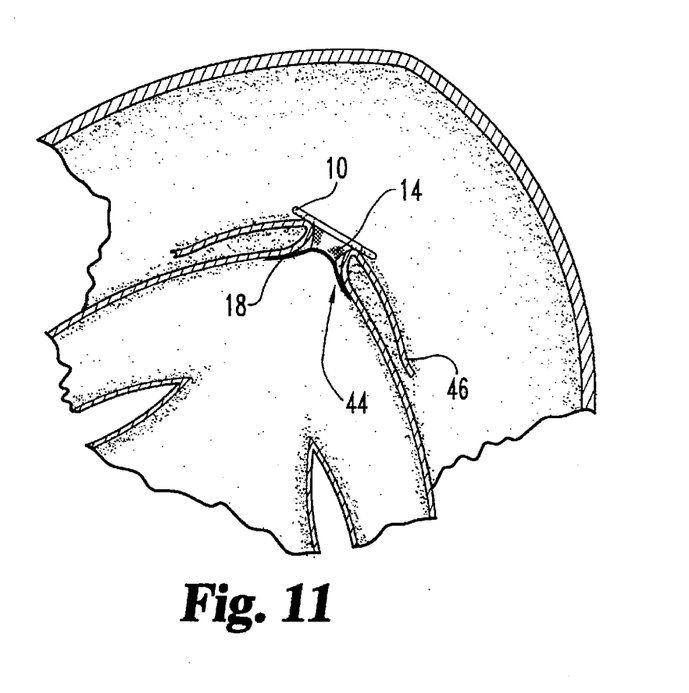
FIG. 11 is a partial cross-sectional view of the disk prosthesis of FIG. 1 in place and sealing across a cardiovascular defect.

After the disk is in place and seated, the filaments are released from the proximal end 32 of catheter 28 and pulled completely free of the catheter by further extending ring 34. When the filaments are released, wire segments 18 resiliently self-expand against the vessel walls into a second larger operational form for restraining disk 10 across the defect.

As the wire segments 18 expand, diaphragm 14 is pulled away from disk 10 and partially through defect opening 44, thereby exerting a compressive force which traps and centers disk 10 across opening 44. As such, disk 10 self-centers across opening 44 to ensure its proper placement.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A flexible closure prosthesis and transcatheter delivery system, wherein said closure prosthesis is adapted to seal across an opening of a fluid passageway within a living body, comprising:

a flexible sealing element;

a flexible restraining element attached to said sealing element, said sealing element and said restraining element defining an integral closure prosthesis prior to delivery across the opening;

a hollow sheath;

a pusher catheter slidable within said sheath; filament means for resiliently bending said closure prosthesis, said filament means releasably connecting said closure prosthesis to said pusher catheter;

said closure prosthesis being resiliently compressible into a first insertion form constrained within said sheath for delivery adjacent the opening, said closure prosthesis resiliently expanding after release from said sheath into a first operational form large than said first insertion form;

said closure prosthesis being resiliently compressible into a second insertion form constrained by said filament means for placement across the opening, said closure prosthesis resiliently expanding after release from said filament means into a second operational form larger than said second insertion form, wherein said sealing element seals across the opening and said restraining element restrains said closure prosthesis in place across the opening;

said flexible sealing element comprising a flexible ring having an opening therethrough and a flexible diaphragm attached to said ring and covering said opening; and said flexible restraining element comprising a plurality of hollow flexible wire segments attached to said diaphragm.

2. The flexible closure prosthesis and transcatheter delivery system of claim 1 wherein said flexible ring further comprises a plurality of flexible elements attached across said ring.

3. The flexible closure prosthesis and transcatheter delivery system of claim 2 wherein:

said flexible ring is constructed from a length of coiled wire resiliently bent into a ring and attached at its ends and includes two to three loops of flexible safety wire inside said coiled wire;

said flexible elements are constructed of elastic filaments tied across said coiled wire;

said flexible diaphragm is constructed from a double wall nylon mesh attached to said flexible ring and containing a flexible foam core therein;

said hollow flexible wire segments are discrete lengths of coiled wire, each wire being attached along a portion of its length to said diaphragm.

4. The flexible closure prosthesis and transcatheter delivery system of claim 1 wherein:

said flexible ring is constructed from a length of coiled wire resiliently bent into a ring and attached at its ends and includes two to three loops of flexible safety wire inside said coiled wire;

said flexible diaphragm is constructed from a double wall nylon mesh attached to said flexible ring and containing a flexible foam core therein;

said hollow flexible wire segments are discrete lengths of coiled wire, each wire being attached along a portion of its length to said diaphragm.

5. The flexible closure prosthesis and transcatheter delivery system of claim 1 wherein said filament means comprises:

a pull ring, said pull ring being larger in diameter than said pusher catheter to prevent passage therethrough;

a plurality of filaments corresponding to said plurality of hollow flexible wire segments, at least one of said filaments routed through one of said wire segments and each of said filaments connected at one end to said pusher catheter and at another end to said pull ring; and wherein pulling of said pull ring causes said filaments to resiliently compress said wire segments.

6. The flexible closure prosthesis and transcatheter delivery system of claim 5 wherein said filaments are monofilaments constructed of nylon.

7. The flexible closure prosthesis and transcatheter delivery system of claim 1 wherein:

said pusher catheter is a double lumen catheter having an inner lumen and an outer lumen; said pusher catheter has a proximal end and an opposite distal end; and said filament means comprise a plurality of filaments coupled to said pusher catheter, said plurality of filaments routed through one of said inner lumen and said outer lumen as said plurality of filaments extend from said proximal end of said pusher catheter to said flexible restraining element and continuing through the outer of said inner lumen and said outer lumen to said proximal end of said pusher catheter to couple said closure prosthesis to said pusher catheter.

8. The flexible closure prosthesis and transcatheter delivery system of claim 1 wherein said filament means comprises:

a pull ring, said pull ring being larger in diameter than said pusher catheter to prevent passage therethrough;

a plurality of filaments corresponding to said plurality of said hollow wire segments, at least one of said filaments routed through one of said wire segments and each of said filaments connected at one end to said pusher catheter and at another end to said pull ring; and wherein pulling of said pull ring causes said filaments to resiliently compress said wire segments.

9. The flexible closure prosthesis and transcatheter delivery system of claim 8 wherein:

said pusher catheter is a double lumen catheter having an inner lumen and an outer lumen; and said filaments attach at an end of said pusher catheter opposite said closure prosthesis and are routed through said outer lumen to said closure prosthesis, through said hollow wire segments, and through said inner lumen to attach to said pull ring.

10. A method for delivering a closure prosthesis for sealing across an opening of a fluid passageway within a living body, comprising the steps of:

connecting a closure prosthesis to a pusher catheter, said closure prosthesis including a flexible sealing element and a flexible restraining element attached thereto;

inserting said closure prosthesis and said pusher catheter into a sheath adjacent the opening, said closure prosthesis resiliently compressing into a first insertion form constrained within said sheath;

releasing said closure prosthesis from said sheath adjacent the opening, said closure prosthesis resiliently expanding into a first operational form larger than said first insertion form adjacent the opening;

resiliently compressing said closure prosthesis into a second insertion form, said restraining element being resiliently compressed to permit passage thereof through the opening;

releasing said closure prosthesis from said pusher catheter, said closure prosthesis expanding into a second operational form larger than said second insertion form, wherein said sealing element seals across the opening and said restraining element restrains said closure prosthesis in place across the opening.

11. A closure prosthesis and transcatheter delivery system for sealing an opening in a fluid passageway within a living body, comprising:

a resiliently flexible sealing element;

at least one flexible restraining element fixedly attached and extendable along one side of said sealing element, said restraining element and said sealing element defining an integral closure element;

said integral closure element compressable into a reduced insertion form suitable for insertion through the fluid passageway and the opening but tending to resiliently assume a relatively thin shape with a surface area sufficiently large to cover the opening;

said fixedly attached restraining element deformable into a reduced insertion form suitable for insertion through the fluid passageway and the opening but tending to resiliently assume a configuration extending adjacent said one side of said sealing element such that said integral closure element pinches an edge of the opening between a portion of said restraining element and said sealing element;

a hollow sheath sized to fit through the opening and having a proximal end;

a pusher catheter slidable within said sheath; and at least one filament slidably connected to said at least one restraining element and having ends extending proximally from said proximal end of said sheath.

12. The closure prosthesis and transcatheter delivery system of claim 11 wherein said at least one flexible restraining element is at least one hollow cylinder; and said at least one filament is threaded through said hollow cylinder.

13. The closure prosthesis and transcatheter delivery system of claim 11 wherein said sealing element is disk shaped.

14. The closure prosthesis and transcatheter delivery system of claim 11 wherein said sealing element has a center portion; and said at least one flexible restraining element is attached to said center portion of said sealing element.

15. The closure prosthesis and transcatheter delivery system of claim 11 wherein each of said at least one flexible restraining element is configured to be longer than the diameter of the opening.

16. The closure prosthesis and transcatheter delivery system of claim 11 wherein said sealing element comprises a resiliently flexible ring and a flexible diaphragm attached across said ring.

17. The closure prosthesis and transcatheter delivery system of claim 11 wherein said sealing element tends to resiliently assume a planar configuration.

18. The closure prosthesis and transcatheter delivery system of claim 11 wherein said pusher catheter has two lumens; and each end of said at least on filament is threaded through a different one of said two lumens.

19. A flexible closure prosthesis and transcatheter delivery system, wherein said closure prosthesis is adapted to seal across an opening of a fluid passageway within a living body, comprising:

a flexible sealing element;

a flexible restraining element attached to said sealing element, said sealing element and said restraining element defining an integral closure prosthesis prior to delivery across the opening;

a hollow sheath;

a pusher catheter slidable within said sheath;

filament means coupling said closure prosthesis and said pusher catheter for bending said flexible restraining element;

said closure prosthesis deformable into a first insertion form constrainable within said sheath for delivery adjacent the opening, said closure prosthesis being resiliently expandable upon release from said sheath into a first operational form that is larger than said first insertion form; and said flexible restraining element deformable into a second insertion form constrained by said filament means, said flexible restraining element resiliently expanding upon release of the constraint of said filament means into a second operational form that is larger than said second insertion form, wherein said sealing element seals across the opening and said restraining element restrains said closure prosthesis across the opening.

* * * * *

UNITED STATES PATENT AND TRADEMARK OFFICE
CERTIFICATE OF CORRECTION

PATENT NO. : 5,643,317
DATED : July 1, 1997
INVENTOR(S) : Dusan Pavcnik et al.

Figure 2A:
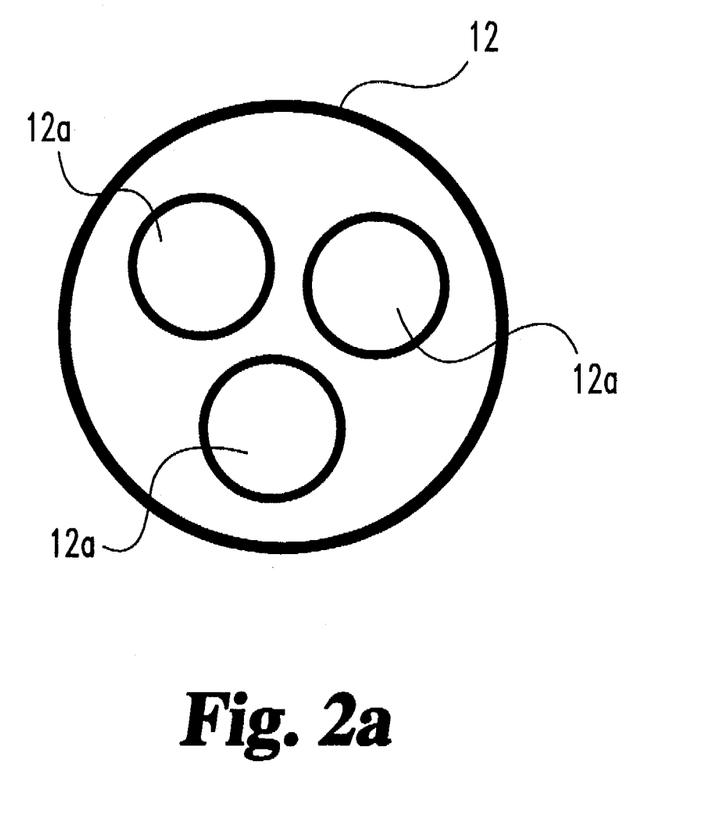

It is certified that error appears in the above-identified patent and that said Letters Patent is hereby corrected as shown below:

Column 2,
Line 41, please change "tile" to -- the --.
Line 44, before "FIG. 3", please insert the following:
-- FIG. 2a is an illustrative sectional view of one embodiment of the ring comprising a portion of the closure prosthesis. --.

Column 4,
Line 35, "As" should begin a new paragraph.
Line 50, "Disk" should be a new paragraph.

Column 5,
Line 14, please change "end" to -- and --.
Line 29, "Referring" should begin a new paragraph.
Line 35, please change "back" to -- out --.

Column 6,
Line 15, "filament" should begin a new paragraph.

Column 9,
Line 1, please change "on" to -- one --.

Signed and Sealed this

Fourteenth Day of June, 2005

JON W. DUDAS
*Director of the United States Patent and Trademark Office*